United States Patent [19]

Plueddemann

[11] Patent Number: 4,718,944
[45] Date of Patent: Jan. 12, 1988

[54] COUPLING AGENT COMPOSITIONS

[75] Inventor: Edwin P. Plueddemann, Midland, Mich.

[73] Assignee: Dow Corning Corporation, Midland, Mich.

[21] Appl. No.: 916,260

[22] Filed: Oct. 7, 1986

[51] Int. Cl.$^4$ .......................... C08K 5/09; C08K 5/54; C08K 9/06

[52] U.S. Cl. ........................... 106/287.11; 106/287.1; 106/316; 523/213; 523/216

[58] Field of Search ................ 106/287.11, 287.1, 316; 523/213, 216

[56] References Cited

U.S. PATENT DOCUMENTS 3,837,876 9/1974 Mayuzumi et al. ............ 106/287.11
4,154,638 5/1979 Franz et al. ..................... 106/287.11
4,339,565 7/1982 Tomoda ......................... 106/287.11

Primary Examiner—Allan M. Lieberman
Attorney, Agent, or Firm—Robert L. McKellar

[57] ABSTRACT

A coupling agent composition comprised of the reaction product of (a) about two mole parts of maleic anhydride with (b) about one mole part of a diamine functional silane compound of the general formula

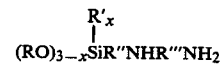

where R denotes an alkyl radical, R' denotes an alkyl radical, R" and R'" denote alkylene radicals and x is 0 or 1; and (c) sufficient solvent to solubilize (a) and (b).

4 Claims, No Drawings

COUPLING AGENT COMPOSITIONS

BACKGROUND OF THE INVENTION

Composite materials which comprise an organic resin and an inorganic filler have been known and used for a number of years. Adhesion stability between the filler and the resinous mixture has been recognized as a source of degradation and failure of these materials for nearly as long as composite materials have been known. Coupling agents are additives which promote adhesion between the filler and resin and improve the hydrolytic stability of the bond between the two. Coupling agents in general have been known and used commercially since the introduction of chromium based coupling agents in the 1950s. Since the introduction of these coupling agents, there has been a steady development of new coupling agents which provide better strength and/or hydrolytic stability with various resin/filler combinations. The actual coupling capability of state of the art coupling agents is quite satisfactory. However, in general the best coupling agents in regards to adhesion and hydrolytic stability are also the most expensive coupling agents. Therefore, any coupling agent composition which gives premium performance at lower costs must be considered an advance in the art.

Surprisingly, it has been found that the addition of maleic anhydride, in certain proportions, to diamino functional silane coupling agents improves the performance of these silanes as coupling agents. Thus, a more effective coupling agent is provided which has the added advantage of being comprised of a substantial proportion of a low cost component (the maleic anhydride).

Aminofunctional silanes are well known in the art as effective coupling agents for epoxide, phenolic, melamine, furane, isocyanate, and other thermosettable resins. The reaction products of organic acids with aminofunctional silanes is also known in the art. For instance, U.S. Pat. No. 3,249,461 granted to Grotenhuis May 3, 1966 teaches the reaction product of an aminofunctional silane coupling agent with an acid chloride or anhydride in one to one amino to acid ratios. All of Grotenhuis's products are 1 to 1 amino radical to carboxy radical products, and are taught to be effective primers or coupling agents for olefinic resins.

U.S. Pat. No. 3,558,741 issued to Holub, et al. Jan. 26, 1971 teaches curable imido substituted organopolysiloxane compositions. Holub's compositions are the reaction product of one mole part aminofunctional silane and one mole part of an unsaturated anhydride such as maleic anhydride. The reaction is run to completion to form imides which Holub teaches are curable compositions.

U.S. Pat. No. 3,773,607 issued to Marzocchi Nov. 20, 1973 teaches silyl amides as "binding agents" between glass fibers or fillers and elastomers. Marzocchi's "anchoring agents" are the reaction product of a carboxy functional silane and an organic amine or an amino functional silane, where the ratio of carboxy groups to amine groups is between 0.8 and 3. Marzocchi does not mention stabilizing the resulting coupling agent composition.

SUMMARY OF THE INVENTION

The present invention is a coupling agent composition comprised of the reaction product of (a) about two mole parts of maleic anhydride; with (b) about one mole part of a diamine functional silane compound of the general formula

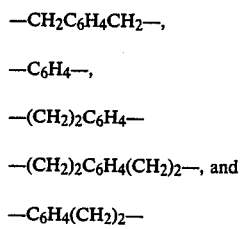

where R denotes an alkyl radical with 1 to 6 carbon atoms or an alkoxyalkyl radical with 2 to 8 carbons, R' denotes an alkyl radical with 1 to 6 carbon atoms, R" and R'" denote alkylene radicals with 1 to 6 carbon atoms, or arylalkylene radicals, alkylarylene radicals or arylene radicals with 6 to 10 carbon atoms, and x is 0 or 1; and a solvent in sufficient quantity to solubilize (a) and (b). R" and R" radicals include divalent radical represented by the following formula:

—CH$_2$C$_6$H$_4$CH$_2$—,

—C$_6$H$_4$—,

—(CH$_2$)$_2$C$_6$H$_4$—

—(CH$_2$)$_2$C$_6$H$_4$(CH$_2$)$_2$—, and

—C$_6$H$_4$(CH$_2$)$_2$—

These radicals can be ortho, meta or para isomers of the above formulae.

These compositions are particularly useful as coupling agents in the production of thermoplastic composite materials and unsaturated polyester composite materials. The compositions can also be used as primers in adhering thermoplastic resins or unsaturated polyester resins to various substrates.

DETAILED DESCRIPTION OF THE INVENTION

The silane compounds used in the present invention include the following silanes; N-(2-aminoethyl)-3-aminopropyltrimethoxysilane, N-(2-aminoethyl)-3-aminopropyltriethoxysilane, N-(2-aminoethyl)-3-aminopropylmethyldimethoxysilane, N-(2-aminoethyl)-3-aminopropyltris(2-ethylhexoxy)silane, p(2-trimethoxysilylethyl)-N-(2-aminoethyl)benzylamine, and N-(3-aminopropyl)-3-aminopropyltrimethoxysilane. These silanes are available commercially. Maleic anhydride is, of course, widely available in commercial quantities, as are the solvents used in the present invention.

Solvents which have been found useful in the present invention include dimethylsulfoxide, sulfolane, butyrolactone, 2-nitropropane, dimethylformamide, methylbutenol, methylbutynol, t-butanol, isopropylalcohol, methyl pyrrolidone, diethylcarbonate, and water. Other solvents may be used as long as they provide sufficient compatibility with the substrate to allow uniform coatings to be formed on the substrate, and provide a solvent which keeps the amine groups of the silane from adding across the double bond of the maleic anhydride. Such addition results in gelation of the composition and reduced effectiveness of the composition as a coupling agent.

The mole ratio of maleic anhydride to diaminofunctional silane is critical in the present invention. If a molar excess of anhydride is not present addition across the maleic anhydride's double biond by the amine functionality of the silane occurs with the result that the mixture gels. As a practical matter, gelation prevents the mixture from being an effective coupling agent. Thus, to avoid the addition across the double bond, sufficient maleic anhydride must be present to form amide-acid products with each of the amino groups of the diamino functional silane. In general, it was found that the anhydride to silane mole ratio should be about 1.7 to about 2.

The compositions of the present invention can be used as coupling agents in composite materials, or as primers in the production of film laminates and such. As will be appreciated by those skilled in the art, the manner in which the present compositions are applied to the substrates can vary depending upon the particular application. For instance, when the present compositions are used as a coupling agent in the production of fiberglass laminates, the compositions can be applied to the fiberglass as dilute solutions, which are then dried before the resin is applied to the treated glass. Alternately, a concentrated solution of the coupling agent composition could be added to the resin which would then be applied to the glass fiber to form the desired composite.

When the compositions of the present invention are used to treat fillers in the production of composites, the amount of the composition used, based upon combined weight of the silane and maleic anhydride, can range from about 0.01 to 2 weight percent based upon the weight of the filler. When used as an additive in filled composites, the composition should comprise between 0.1 and 2 weight percent of the filler. When used as a primer the composition can be applied effectively as a 0.1 to 10 wt% solids solution to the solid substrate.

The compositions of the present application are useful as primers and coupling agents for widely varied combinations of thermoplastics and substrates. These thermoplastics include polyethylene, polypropylene, polycarbonate, polystyrene, acrylonitrile butadiene styrene terpolymer, modified polyethylene, polyurethane, nylon and various copolymers. The compositions of the present invention can also be used effectively as coupling agents for unsaturated polyester resins.

The substrates and fillers which can be effectively coupled or bonded to the aforementioned resins include inorganic fillers such as glass, quartz, ceramic, asbestos, silicone resin and glass fibers, metals such as aluminum, steel, copper, nickel, magnesium, and titanium, metal oxides such as MgO, $Fe_2O_3$, and $Al_2O_3$, and metal fibers and metal coated glass fibers. Substrates which can be effectively primed using the present compositions include metal foils and glass.

As mentioned, the mixture of maleic anhydride and diamino functional silane of the present application will react to some extent in solution. Where the silane used is N-(2-aminoethyl)-3-aminopropyltrimethoxysilane, the reaction products expected are represented by the formulae:

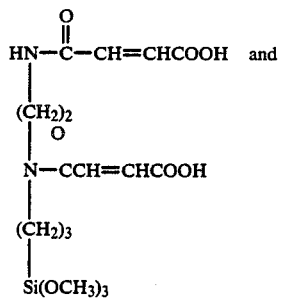

1.

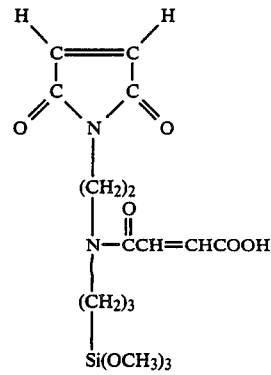

2.

The solutions will be comprised predominantly of the amide represented by Formula 1, with a small proportion of the imide product represented by Formula 2, also present.

EXAMPLES

The following examples illustrate the effectiveness of the present invention relative to state of the art coupling agents and primers. The examples do not fully illustrate the scope of the invention and should not be understood as delineating the limits of the invention.

EXAMPLE 1

This example illustrates the criticality of the mole ratio of maleic anhydride to N-(2-aminoethyl)-3-aminopropyltrimethoxysilane to the stability of the reaction product. Several 20 wt% solutions of maleic anhydride and N-(2-aminoethyl)-3-aminopropyltrimethoxysilane in isopropanol were made which varied in their anhydride to silane ratio as indicated in Table 1. As can be seen from the solution stability tests performed on these solutions only the 2:1 anhydride:silane solution was stable for a significant period. The other solutions formed either gels or precipitates, neither of which would be effective coupling agents.

TABLE 1

| Maleic Anhydride Silane Ratio | Gelation Time |
|---|---|
| 1:1 | 3 days |
| 1.5:1 | 7 days |
| 2:1 | stable after three months |

Solution stability tests were also conducted in isopropanol under accelerated aging conditions. The various solutions were kept at 50° C. These results indicated that the most stable maleic anhydride/N-(2-aminoethyl)-3-aminopropyltrimethoxysilane solutions were those with an anhydride to silane ratio greater than or equal to 1.75/1.

EXAMPLE 2

This example demonstrates the effectiveness of the present product as a coupling agent in micro Novacite filled polyester composites. Novacite, a form of low quartz, was treated with various coupling agents at the level of 0.25 wt% coupling agent based upon the weight of the treated Novacite. The coupling agents used were (1) a 2:1 mole mixture of maleic anhydride and N-(2-aminoethyl)-3-aminopropyltrimethoxysilane; (2) vinyltrimethoxysilane; (3) 3-methacryloxypropyltrimethoxysilane; (4) 3[2(vinyl-benzylamino)ethylamino]propyl-trimethoxysilane; and (5) a control using no coupling agent. The fillers were compounded with equal weight parts of an unsaturated polyester resin (CoResyn® 5500 sold by Interplastics Corp. of Minneapolis, Minn.). The compounded mixtures were cast into rods, cured at 100° C. for 24 hours, cooled, and the flexural strength of each sample rod was measured over a two inch span according to standard test procedures. New samples were made and their flexural strength was measured after being boiled for 24 hours in water. The test results are presented in Table 2.

TABLE 2

| Coupling Agent | Flexural Strength (psi) | |
|---|---|---|
|  | Dry | 24 Hr. Boil |
| 1 | 20100 | 14900 |
| 2 | 15400 | 11900 |
| 3 | 18800 | 14700 |
| 4 | 20700 | 16500 |
| 5 | 12800 | 9800 |

These results indicate the invention composition (#1) is a more effective coupling agent than the commercial coupling agents, except for coupling agent (4) a premium silane which costs more than #1. The inventive coupling agent was nearly as effective as the premium cost coupling agent.

EXAMPLE 3

This example demonstrates the effectiveness of the present invention as a primer for various thermoplastics to glass. Glass slides were coated with 20 wt% solutions of various coupling agents, and dried to form primed slides. Molten thermoplastics were then applied to the primed surfaces and cooled. The cooled slides were then immersed in water until the thermoplastic film no longer adhered to the slide. Since hydrolytic stability is an accurate indicator of the strength of the bond between the thermoplastic and the glass, the samples which had the longest time to failure upon immersion in water were considered to have the best adhesion.

The various silane coupling agent compositions used in this example were:
1. N-(2-aminoethyl)-3-aminopropyltrimethoxysilane;
2. 3-methacryloxypropyltrimethoxysilane;
3. 3[2-(vinylbenzylamino)ethylamino]propyltrimethoxysilane;
4. 3-glycidoxypropyltrimethoxysilane;
5. 3-aminopropyltrimethoxysilane; and
6. the reaction product of 2 mole parts maleic anhydride with 1 mole part N-(2-aminoethyl)-3-aminopropyltrimethoxysilane.

The various types of thermoplastics used in this example were polyethylene (P.E.), polypropylene (P.P.), polystyrene (P.S.), acrylonitrile-butadiene-styrene terpolymer (ABS), modified polyethylene (sold as Plexar-6® by Chemplex Company, Rolling Meadows, IL). (MPE), polyurethane (PU), polybutylene terephthalate (PBT), nylon, polycarbonate (PC), and polyether ether ketone (PEEK). The results of the tests are summarized in Table 3a and 3b.

Each of the thermoplastics had a unique capacity to bond to the primed glass samples. Therefore, each set of ratings is relative to the type of thermoplastic used in the sample. Within each type of thermoplastic the samples were rated based upon the strength and hydrolytic stability of the bond between the thermoplastic. Samples with the best adhesion and stability were rated +++, samples with the worst adhesion and stability were rated −. The relative performance of each sample was based upon comparisons with the other listed coupling agent compositions. For instance, in the case of an SBR block copolymer, Kraton® sold by Shell Chemicals of Houston, TX the following results were achieved.

| Coupling Agent | Peel Strength (N/cm) Upon Immersion in Boiling Water | | | |
|---|---|---|---|---|
|  | 1 hr. | 2 hrs. | 6 hrs. | 10 hrs. |
| 1 | c | 3.5 | nil | — |
| 2 | c | 12 | 5.2 | nil |
| 3 | c | 1.7 | nil | — |
| 4 | 0.5 | nil | — | — |
| 5 | 0.5 | nil | — | — |
| 6 | c | c | c | c |

Note:
c denotes cohesive failure of the thermoplastic, ie. the bond was stronger than the thermoplastic itself.

These results correspond to the following ratings: coupling agents 1, 2 and 3 would be rated +; coupling agents 4 and 5 would be rated −; and coupling agent 6 would be rated +++.

TABLE 3a

| Coupling Agent | Thermoplastic | | | | |
|---|---|---|---|---|---|
|  | PE | PP | PS | ABS | MPE |
| 1 | − | − | − | + | − |
| 2 | + | − | − | − | − |
| 3 | ++ | ++ | ++ | ++ | + |
| 4 | − | − | − | − | + |
| 5 | − | − | + | − | − |
| 6 | ++ | + | + | ++ | + |

TABLE 3b

| Coupling Agent | Thermoplastic | | | | |
|---|---|---|---|---|---|
|  | PU | PBT | Nylon | PC | PEEK |
| 1 | − | − | − | + | − |
| 2 | − | − | + | + | − |
| 3 | ++ | ++ | + | + | + |
| 4 | ++ | ++ | + | + | − |
| 5 | − | − | − | + | − |
| 6 | ++ | ++ | + | ++ | ++ |

The results of the tests indicate that the invention composition is an effective primer for a variety of types of thermoplastics. Only 3[2-(vinylbenzylamino)ethylamino]-propyltrimethoxysilane is as widely effective as a primer as the invention composition per the test method employed.

EXAMPLE 4

This example demonstrates the effectiveness of the present invention as a primer for epoxy resin to glass. Glass slides were coated with 20 wt% solutions of various coupling agent compositions, and dried. A film of an epoxy adhesive (Magnabond-6388-3 sold by Magnolia Plastics of Chamblee, GA) was applied to the primed slides and cured at 70° C. for 2 hours. After cooling, samples were immersed in 60° C. water and the time until failure of the bond between the resin and the glass slide was measured. The results are presented in Table 4.

TABLE 4

| Primer | Time to Adhesive Failure |
| --- | --- |
| none | 1 hr. |
| 3-aminopropyl trimethoxysilane | c |
| N—(2-aminoethyl)-3-amino-propyltrimethoxysilane | 8 hr. |
| 3[2(vinylbenzylamino)ethylamino]propyl trimethoxy silane | c |
| 3-glycidoxypropyltrimethoxysilane | 2 hr. |
| reaction product of 2 m maleic anhydride with 1 m N—(2-aminoethyl)-3-amino-propyltrimethoxysilane | c |

Note:
c denotes that the epoxy was adhered to the glass slide even after 24 hours of immersion in water.

The results of this comparison show that the reaction product of 2 mole parts maleic anhydride with 1 part N-(2-aminoethyl)-3-amino-propyltrimethoxysilane adheres the epoxy resin to the glass slide more effectively than N-(2-aminoethyl)-3-amino-propyltrimethoxysilane alone, or 3-glycidoxypropyltrimethoxysilane.

EXAMPLE 5

This example demonstrates the effectiveness of the present invention as a primer for unsaturated polyester resin to glass. Glass slides were primed using 20 wt% solutions of the silanes described in Example 3. An unsaturated polyester resin with 0.5 wt% dicumyl peroxide (CoResyn® 5500 sold by Interplastic Corp. of Minneapolis, Minn.) was applied to the various primed slides and cured at 100° C. for 24 hours. The slides were cooled, then immersed in 70° C. water until the polyester resin film no longer adhered to the slide. The 2 maleic anhydride: 1N-(2-aminoethyl)-3-amino-propyl-trimethoxysilane product gave the most effective and hydrolytically stable adhesion of the polyester resin to the glass slide.

| CoResyn ® 5500 Adhesive to Primed Glass (time to failure in 70° C. H₂O in hours) | |
| --- | --- |
| Primer on Glass | Time to Failure (hrs) |
| None | <1 |
| vinyltrimethoxysilane | 3 |
| 3[2(vinylbenzylanimo)-ethylamino] propyltri-methoxysilane | 6 |
| 3-methacryloxypropyl trimethoxysilane | 12 |
| 3-glycidoxypropyl-trimethoxysilane | 6 |
| N—(2-aminoethyl)-3-aminopropyltri-methoxysilane + 2 mole parts maleic anhydride | 10 |

What is claimed is:

1. A composition comprising:
(A) the reaction product of about (i) 1.7 to 2 mole parts maleic anhydride with (ii) 1 mole part of a silane represented by the general formula

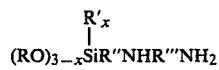

where
R denotes an alkyl radical with 1 to 6 carbon atoms or an alkoxyalkyl radical with 2 to 8 carbons,
R' denotes an alkyl radical with 1 to 6 carbon atoms,
R" and R''' denote alkylene radicals with 1 to 6 carbon atoms, or alkylarylene radicals, arylalkylene radicals, or arylene radicals with 6 to 10 carbon atoms and x is 0 or 1, and
(B) sufficient solvent to solubilize (A).

2. The composition of claim 1 wherein the silane (ii) is N-(aminoethyl)-3-aminopropyltrimethoxysilane.

3. The composition of claim 1 wherein the solvent is chosen from the group consisting of butyrolacetone, 2-nitropropane, dimethylformamide, t-butanol, methyl butenol, methylbutynol, isopropanol, diethylcarbonate, and methylpyrrolidone.

4. The composition of claim 1 wherein the solvent is water.